(12) United States Patent
Laniado et al.

(10) Patent No.: US 7,959,550 B2
(45) Date of Patent: Jun. 14, 2011

(54) METHOD AND APPARATUS FOR POTENTIATING PENILE ERECTION UTILIZING ULTRAWEAK ELECTROMAGNETIC FIELD OF VERY LOW FREQUENCY

(76) Inventors: Shlomo Laniado, Tel Aviv (IL); Zvi Kamil, Tel Aviv (IL)

( * ) Notice: Subject to any disclaimer, the term of this patent is extended or adjusted under 35 U.S.C. 154(b) by 1506 days.

(21) Appl. No.: 11/320,346

(22) Filed: Dec. 28, 2005

(65) Prior Publication Data
US 2006/0189839 A1   Aug. 24, 2006

Related U.S. Application Data

(60) Provisional application No. 60/639,468, filed on Dec. 28, 2004.

(51) Int. Cl.
*A61N 1/00* (2006.01)
(52) U.S. Cl. ............................................................ 600/14
(58) Field of Classification Search ............... 600/9–15, 600/29–30, 38; 128/844, 897, 899
See application file for complete search history.

(56) References Cited

U.S. PATENT DOCUMENTS

| 5,269,746 | A | | 12/1993 | Jacobson | |
|---|---|---|---|---|---|
| 5,366,435 | A | | 11/1994 | Jacobson | |
| 5,509,888 | A | | 4/1996 | Miller | |
| 5,571,118 | A | * | 11/1996 | Boutos | 607/138 |
| 5,598,587 | A | | 2/1997 | Wada | |
| 5,682,901 | A | | 11/1997 | Kamen | |
| 5,984,854 | A | * | 11/1999 | Ishikawa et al. | 600/9 |
| 5,992,233 | A | | 11/1999 | Clark | |
| 6,004,257 | A | | 12/1999 | Jacobson | |
| 6,032,531 | A | | 3/2000 | Roszhart | |
| 6,050,959 | A | | 4/2000 | Card | |
| 6,099,459 | A | | 8/2000 | Jacobson | |
| 6,164,134 | A | | 12/2000 | Cargille | |
| 6,238,333 | B1 | * | 5/2001 | Loos | 600/9 |
| 6,292,695 | B1 | | 9/2001 | Webster | |
| 6,348,033 | B1 | | 2/2002 | Catlett | |
| 6,436,029 | B1 | | 8/2002 | Benderev | |

(Continued)

FOREIGN PATENT DOCUMENTS

WO   WO 97 45702   12/1997

OTHER PUBLICATIONS

Shafik, A., el-Sibai, O., and Shafik, AA. "Magnetic stimulation of the cavernous nerve for the treatment of erectile dysfuntion in humans." International Journal of Impotence Research. vol. 12 (2000): pp. 137-142. <http://web.ebscohost.com/ehost/pdf?vid=2&hid=113 &sid=756b1bc4-c770-4064-8823-ae862046d788%40sessionmgr109>.*

(Continued)

*Primary Examiner* — Charles A Marmor, II
*Assistant Examiner* — Christine D Hopkins
(74) *Attorney, Agent, or Firm* — Ostrager Chong Flaherty & Broitman P.C.

(57) ABSTRACT

An apparatus and method for treating erectile dysfunction by using a pulsating, ultraweak, magnetic field. A transducer generates an ultraweak, pulsating magnetic fields which is applied to the penis, which as a result of the magnetic field causes the erection of the penis. Another aspect of the invention is an apparatus and method for treating medical conditions in women by using a pulsating, ultraweak, magnetic field.

3 Claims, 3 Drawing Sheets

U.S. PATENT DOCUMENTS

| | | | |
|---|---|---|---|
| 6,443,883 B1* | 9/2002 | Ostrow et al. | 600/14 |
| 6,482,147 B2 | 11/2002 | Knoll-Ewers | |
| 6,485,408 B2* | 11/2002 | Orten | 600/38 |
| 6,564,096 B2 | 5/2003 | Mest | |
| 6,589,159 B2 | 7/2003 | Paturu | |
| 6,676,591 B2 | 1/2004 | Price | |
| 6,885,895 B1* | 4/2005 | Whitehurst et al. | 607/39 |
| 6,924,642 B1* | 8/2005 | Cho et al. | 324/240 |
| 2002/0128564 A1 | 9/2002 | Carlson et al. | |
| 2002/0151760 A1* | 10/2002 | Paturu | 600/15 |
| 2004/0206359 A1 | 10/2004 | Shapiro et al. | |
| 2004/0206360 A1 | 10/2004 | Shapiro et al. | |
| 2004/0206361 A1* | 10/2004 | Shapiro et al. | 128/844 |
| 2007/0185541 A1* | 8/2007 | DiUbaldi et al. | 607/41 |

OTHER PUBLICATIONS

Ueno, N. et al. "The effect of sildenafil on electrostimulation-induced erection in the rat model." International Journal of Impotence Research. vol. 14 (2002): p. 251-255. <http://www.nature.com/ijir/journal/v14/n4/pdf/3900860a.pdf>.*

Schwartz et al. "Exposure of Frog Hearts to CW or Amplitude-Modulated VHF Fields: Selective Efflux of Calcium Ions at 16 Hz." Bioelectromagnetics. vol. 11 (1990): p. 349-358.*

Rainer B. Pelka, Ph.D., Christof Jaenicke, M.D., & Joerg Gruenwald, Ph.D., Impulse Magnetic-Field Therapy for Erectile Dysfunction: A Double-Blind, Placebo-Controlled Study, Jan./Feb. 2002, pp. 53-60, vol. 19 No. 1, Germany.

Geiger W et al., New Designs of Micromachined Vibrating Rate Gyroscopes with Decoupled Oscillation Modes, 1997 International Conference on Solid-State Sensors and Actuators, Jun. 16, 1997, pp. 1129-1132, vol. 2, Chicago, Illinois.

Song H et al., Wafter Level Vacuum Packaged De-coupled Vertical Gyroscope by Proceedings of the IEEE, 13th Annual International Conference on Micro Electro Mechanical Systems. Jan. 23, 2000, pp. 520-524, Miyazaki, Japan.

2004, Frenneaux MD, Autonomic changes in patients with heart failure and in post-myocardial infarction patients, http://www.bmj-journals.com/cgi/reprintform, Heart 2004, 90:1248-1255.

Sanderson et al., Effect of beta blockade on baroreceptor and autonomic function in heart failure, Clinical Science, 1999, 96:137-146.

Lanfranchi PA and Somers VK, Arterial baroreflex function and cardiovascular variability: interactions and implications, http://www.ajpregu.org, Am J Physiol Integr Comp Physiol. 2002, 283:R815-R826.

LaRovere et al., Short-term heart rate variability strongly predicts sudden cardiac death in chronic heart failure patients, http://www.circulationaha.org, Circulation, 2003, 107:565-570.

Benjamin Scherlag, William S. Yamanashi, Yuemei Hou, Jerry I. Jacobson, Warren M. Jackman and Ralph Lazzara, Magnetism and Cardiac Arrhythmias, Cardiology in Review: vol. 12(2) Mar./Apr. 2004, pp. 85-96.

* cited by examiner

METHOD AND APPARATUS FOR POTENTIATING PENILE ERECTION UTILIZING ULTRAWEAK ELECTROMAGNETIC FIELD OF VERY LOW FREQUENCY

PRIORITY CLAIM

This non-provisional application claims priority from U.S. Provisional Patent Application Ser. No. 60/639,468 ("Pat. Appl. 60/639,468") filed on Dec. 28, 2004, the disclosures of which are incorporated herein by reference in their entirety.

FIELD OF THE INVENTION

This invention generally relates to the use of magnetic fields to treat medical conditions. More particularly, it relates to an apparatus and method using an ultraweak, pulsed electromagnetic field of very low frequency (below 300 Hz) to potentiate penile erection.

BACKGROUND OF THE INVENTION

Erectile dysfunction ("ED") is defined as a persistent inability to obtain and maintain an erection satisfactory for sexual activity. Many disease states, such as diabetes, hypertension, depression, and vascular disease, are associated with this condition, which may occur many years prior to the onset of these disorders.

The human penis is composed of the glans penis, the corpus spongiosum with the bulb of the penis, and the paired corpora cavernosa in which skeletal muscle structures and the continuing tunica albuginea completely surround and contain smooth muscle structures, which intermingle with fibrous tissue to form the wall of the sinusoids. The corpus spongiosum is partially entrapped by the skeletal muscle. These encased tissues finally pass through and are regulated by the surrounding structures. The penis gives the appearance of being an independent organ because of its skeletal muscle structures. They are the tissues that determine the penile shape as well as an essential part in the establishment of a rigid penis.

The penis mimics the structure of other parts of the human body where skeletal muscles and the skeleton encompass those visceral organs in which smooth muscles reside. It is a pendulous organ that is uniquely suspended from the front and strongly adheres to the pubic ramus and ischium via the tenacious periostium. The organ leans on and is supported by a suspensory ligament that is an extension of the linea alba. The penis should be considered as a specialized vascular organ and an extension of the vascular system.

In the penis, sinusoidal blood vessels are surrounded by a syncytium of vascular smooth muscle cells. These become dysfunctional with aging, resulting in an inability of these smooth muscle cells to relax normally following sexual stimulation. This is what primarily leads to the development of erectile dysfunction.

Different types of drugs, including phosphodiesterase (PDE) inhibitors, β-adrenergic receptors, and adenylate cyclase activators, have been used to treat ED, with varying degrees of success. The phenomenal success of sildenafil (Viagra®) in improving erections in men with erectile dysfunction is due to the fact that this drug, as a phosphodiesterase inhibitor, improves the relaxation of smooth muscle cells, which become dysfunctional with the aging process. However, not everyone responds to this medication, mainly because the efficacy of the drug is directly dependent on the release of nitric oxide ("NO") from the nerve terminals of the cavernosal nerve, and this may become defective with aging or certain disease states. Many men do not respond to sildenafil and lack of efficacy is a much more common reason for discontinuation than side effects.

This is further elucidated when describing the mechanism of normal erection.

Erection occurs due to the relaxation of tonically constricted helicine arteries (branches of the cavernous artery) and relaxation of cavernosal smooth muscle cells (SMCs). These vasodilator events flood lacunars spaces ("sinusoids") in the paired corpora cavernosa with blood at arterial pressure. The intracavernosal pressure of the engorged penis is raised above systemic arterial pressure by the action of the ischiocavernosus muscles. The expansion of the corpora is restricted by a thick fibrous coat, the tunica albuginea, so that during erection, the venous channels draining the sinusoids are crimped, preventing venous drainage and thereby sustaining tumescence.

In general, stimuli that promote penile SMCs relaxation cause erection and those that cause constriction of penile SMCs cause detumescence. As discussed in more detail below emerging evidence suggests that impairment of potassium ion ("$K^+$") channel activity in cavernosal and arterial SMCs or reduced passive conductance of electrical signals in SMCs can lead to ED.

Smooth muscle relaxation during erection depends upon the promotion of calcium ion ("$Ca^{2+}$") efflux out of the smooth muscle cells. This relaxation of smooth muscle cells is mediated mainly by nitric oxide, which activates the enzyme guanylate cyclase. This cytoplasmic enzyme increases formation of the second messenger, cGMP. Elevated levels of peripheral cGMP, in turn, promote the opening of sarcolemal $K^+$ channels inducing the efflux secondary of $Ca^{2+}$ ions from the cavernosa smooth muscle cells to induce muscle relaxation, facilitate blood flow into the corpora cavernosa, and thereby help obtain, and maintain penile erection. Under physiological conditions the process of penile detumescence, mediated by efferent sympathetic pathways, follows the tumescence phase. Adrenergic sympathetic nerves release norepinephrine, which acts on adrenoceptors in penile smooth muscle. This result in reduced arterial inflow, diminished lacunar space volume and accelerated corporeal venous outflow. The flaccid state of the penis is maintained by contraction of penile smooth muscle cells mediated by the intracellular accumulation of $Ca^{2+}$ ions.

Despite the fact that the metabolic rate of corporal smooth muscles has not been reported yet, the penis, as an external organ, supplies a decreased temperature compared to the mean warmth of the central body (around 34.4° C.). Therefore, its energy requirements can be met at very low blood flow rates. During sexual excitement, the helicine arteries dilate and straighten which, in turn, allows blood to enter directly into the sinusoidal spaces. At that time, there is a 5-10 fold increase in blood flow to the penis, and its temperature rises one or more degrees Celsius.

It is again emphasized that decreased penile vascular resistance induced by corporal smooth muscle relaxation is the most important step in penile erection. The heightened tone of the corporal smooth muscles is considered a major cause of impotence.

Modulation of corporal smooth muscle tone is a complex process requiring the integration of a host of intracellular events and extracellular signals. In intracellular events of corporal smooth muscle cells, the potassium ion channels and calcium ion channels play a major role. Functionally, potassium channels are important regulators of smooth muscle membrane potential in response to depolarizing stimuli and they counteract calcium channels. Potassium channels have been shown to play a fundamental role in both the physiologic and pathophysiologic regulation of smooth muscle tone in diverse tissues.

As with many other smooth muscle cell types, corporal myocyte contractility is inextricably linked to ion channel activity. Corporal smooth muscle cells possess a rich repertoire of ion channels, including calcium, chloride and potassium channels. Among these, are of particular importance, the $K_{ATP}$ channel (i.e., the metabolically regulated $K^+$ channel) and the $K_{Ca}$ channel (i.e., the Maxi-K or large conductance, calcium-sensitive $K^+$ channel).

Ion channel functions are tied together. The opening of potassium channels will lead to the efflux of $K^+$ down its electrochemical gradient and out of the corporal smooth muscle cell. Meanwhile, the opening of calcium channels will produce exactly the opposite effect, that is, the influx of $Ca^{2+}$ down its electrochemical gradient. The former moves positive charge out of the corporal smooth muscle cell and leads to hyperpolarization (i.e., decreased membrane potential), and thus, reduced cellular excitability, primarily by virtue of the corresponding inhibition of transmembrane calcium flux through L-type voltage-dependent $Ca^{2+}$ channels.

The transmembrane movement of $Na^+$, $K^+$, $Ca^{2+}$ and $Cl^-$ ions is a principal pathway by which stimuli to the extracellular membrane are transduced to the cytoplasm. Modified efflux and influx of these ions through specific plasmalemma channels will evoke changes in the membrane potential that are associated with the initiation, modulation or termination of cellular activities.

Voltage-gated ion channels underlie electrical impulses in the surface membranes of excitable cells. The $Na^+$, $K^+$ and $Ca^{2+}$ channels are all composed of homologous repeated domains that form a membrane-spanning pore. They are present in "signal" dependent organisms as low as bacteria, and as high as man. The channels are normally closed when transmembrane voltage is negative inside of the cell, relative to the extracellular space (resting state), but they open when the potential decreases or reverses. The fourth membrane-spanning segment (S4) within each domain contains positively charged residues and is thought to serve as the voltage sensor.

The basic functional behavior of ion channels is based on two fundamental processes: permeation and gating. Permeation is responsible for the selective and efficient translocation of ions across the membrane, whereas gating tightly controls access of ions to the permeation pathway effectively, determining selective channel activity. Ion channels, like many other proteins, have minute moving parts that perform useful functions. Distinct formations are typically characterized by differences in the relative orientations of nearby compact domains linked by hinges or swivels ("linkers") composed of glycine residues or flexible loops. Segments are allowed rotation, and the implied rotations have direct bearing on the functional output since large orientation changes have been discovered in those minute cellular structures to allow them respond to resonant electromagnetic ("EM") pulse.

Structure and Function of Certain Voltage-Gated Channels

As stated, in calcium channels four homologous domains of a single polypeptide are arranged around the permeation pathway. The ion-selective permeation pathway is lined primarily by the four S6 segments and by the extracellular S5-S6 loops. The S5 and S6 segments along with the inclusive S5-S6 linker are sometimes called the pore domain of a subunit or domain. In $Ca^{2+}$ channels the main voltage sensors are the four positively charged S4 segments. Each S4 segment in the $Na^+$ and $K^+$ channels have three to eight basic residues, either arginines or lysines, which are usually separated from each other by two neutral residues. Depolarization is expected to move S4 segments outward through the electric field. One early consequence of this S4 movement is the opening of the activation gate, believed to be formed by the cytoplasmic ends of the channel's four S6 segments, at the entrance of the permeation pathway. Prolonged depolarization also causes the inactivation of the gates by affecting openings located elsewhere in the protein to close (the "ball in the dock" is a possible mechanism).

Closer examination of the periodicity in the energetic perturbations within individual transmembrane segments suggests that at least major portions of all four segments (S1-S4) adopt α-helical structures. In addition, there is evidence for α-helical structure in the two extracellular linkers. The structure of α-helix in protein units of the channel is of outmost significance. It is our belief that through this principal structure, a weak electromagnetic field ("WMF") pulses in stochastic resonance mode, affecting the gating of the channel. It is α-helical segments which; when they slide or rotate, that determine if a channel is in a closed or open position.

In channel function, gating is the essence of the matter, providing the mechanism which transforms information into crucial cellular action. In our observation (pigs, rats, isolated cardiac cells in culture) WMF activates $K_{ATP}$ channels and induces closure of $Ca^{2+}$ channels, thus reducing $Ca^{2+}$ concentration within the myocyte.

In response to a positive change in the transmembrane voltage (defined as intracellular potential minus extracellular potential), the channel will open rapidly in a process called "activation". Immediate return of the potential to the resting level (generally about −70 mV inside) reverses the process, closing the channel (known as "deactivation"). If after activation the positive potential is maintained, the channel will close despite the maintained activating stimulus. This type of closure is called "inactivation". The inactivated channel is generally unresponsive to further activating stimuli unless the membrane is returned to a negative potential, which permits the channel to recover from inactivation and return to the resting closed state.

At any rate, the opening of voltage-gated ion channels is, in most cases, followed by inactivation when the membrane is maintained at a depolarized potential. The inactivation serves a number of important functions: it regulates the membrane excitability ($K^+$ channels), and it prevents $Ca^{2+}$ loading in cells (through $Ca^{2+}$ channels). Most voltage-gated ion channels have a number of different inactivation mechanisms with time constants differing with several orders of magnitudes, from microseconds to minutes. $K_{TAP}$ channels are mostly dormant to be mobilized when metabolically needed. In such events the everage burdting opening fluctuation occurs every (about) 62.5 msec which imply that $K_{TAP}$ channels are in potential "ready" to fire (open) at a frequency of about 16 Hz.

The $K^+$ and $Ca^{2+}$ Channels

The efflux of $K^+$ ions following opening of $K^+$ channels is a mechanism that cells use to maintain or restore a resting state or attenuate the level of depolarizing effects produced by excitatory currents. This occurs because of a shift of the membrane potential towards the equilibrium potential of potassium ("EK", that is, the membrane potential that would be produced if the $K^+$ ions were in equilibrium across the membrane).

With the enormous advances recently made in the elucidation of the architecture and function of $K^+$ channels, they have arguably become the best-understood ion channels. Despite extensive studies, however, they are still full of surprises. Because activation of $K^+$ channels leads to hyperpolarization, regulation of their activity by cellular metabolites may be a particularly important homeostatic mechanism for suppressing electrical activity during periods of overstimulation, cellular damage, hypoxia, or stress. Such is the case in the mechanism of erection.

The distribution of calcium ions across the corporal smooth muscle cell membrane ensures that the opening of calcium channels will lead to the influx of calcium ions into the corporal smooth muscle cell down their electrochemical gradient. As mentioned above, the movement of positive charge into the smooth muscle cell has the opposite effect of the movement of $K^+$ out of the cell, and therefore, will lead to depolarization. Several studies have documented the importance of continuous transmembrane calcium influx through L-type voltage-dependent calcium channels to the sustained contraction of human corporal smooth muscle. Much of the most compelling mechanistic data concerning the role of calcium channels in modulating human corporal smooth muscle tone have been established using digital imaging microscopy of Fura-2-loaded cultured corporal smooth muscle cells.

The inventors used similar imaging techniques in assessing calcium efflux behavior in cardiac cell culture exposed to magnetic fields. These studies have provided strong evidence for the presence, and physiological relevance, of transmembrane calcium flux through the L-type voltage-dependent calcium channel, in response to external artificial activation. There was outward shift of $Ca^{2+}$ from cultured myocyte cells.

When $K^+$ channels are inhibited, the tonic efflux of positively charged $K^+$ ions is diminished. This renders the interior of the cell more positive, resulting in SMC depolarization. The resting Em of vascular SMCs is ~−50 mV. At this potential, the voltage-gated L-type $Ca^{2+}$ channel has a low open-state probability and $Ca^{2+}$ influx is limited to promote relaxation. Thus, $K^+$ channel blockers cause vasoconstriction largely through their ability to depolarize the SMC membrane and thereby open L-type $Ca^{2+}$ channels, which are the major ports for voltage-gated $Ca^{2+}$ entry in SMCs. Conversely, $K^+$ channel openers, (a name applied to a whole and versatile host of agents which posses the ability to facilitate $K_{ATP}$ and $K_{Ca}$ channels) by virtue of causing membrane hyperpolarization, cause vasodilatation. Based on the conventional pharmacological and biophysical nomenclature, the relevant types of $K^+$ channels expressed by most vascular SMCs include $Ca^{2+}$ sensitive $K^+$ ($K_{Ca}$) or maxi channels and ATP-sensitive $K^+$ ($K_{ATP}$) channels. The whole-cell $K^+$ current ($lK^+$), measured by the patch-clamp technique in SMCs is an ensemble current, reflecting the simultaneous activity of at least several $K^+$ channel types, however, in SMCs, $K_{Ca}$ and $K_{ATP}$ are of prime importance.

In general, potassium channel openers ("KCOs") have been identified for the two primary classes of $K^+$ channels: adenosine 5'-triphosphate (ATP)-sensitive $K^+$ channels ($K_{ATP}$) and high conductance $Ca^{2+}$ activated $K^+$ channels ($BK_{Ca}$). The $K_{ATP}$ channels, which belong to the inward rectifier $K^+$ channel superfamily, are regulated by the intracellular ATP concentration; an increase in [ATP]i results in closure of the $K_{ATP}$ channel. The $BK_{Ca}$ (Maxi) channels, which belong to the voltage-dependent $K^+$ channel superfamily, are activated by increases in $[Ca^{2+}]i$ and are sensitive to depolarization. The $BK_{Ca}$ channels and the $K_{TAP}$ channels provide a link between the cell activity and the membrane conductance of $K^+$ ions and, as such, may work as a negative feedback process, especially in highly active cells.

When the abovementioned two potassium channels of big conductance open, changes in the electrical potential across the cell membrane occur and result in a more polarized state. A number of diseases or conditions can take advantage of the hyperpolarization effect on the membrane to reduce cystosolic $Ca^{2+}$ and can be treated with therapeutic agents (i.e., drugs) that open potassium channels (KCOs). Such diseases or conditions include asthma, epilepsy, hypertension, male sexual dysfunction, and female sexual dysfunction.

In penile tissue, there is indeed evidence that NO and cGMP promote hyperpolarization and relaxation of SMCs by opening $BK_{Ca}$ (Maxi K) channels. The $K^+$ channels (e.g. $BK_{Ca}$, and $K_{ATP}$), which appear to be important in normal erectile function, are becoming effective therapeutic targets in treating ED.

Naturally, there also appears to be a role for other classes of $K^+$ channels in erection, including the adenosine triphosphate-sensitive $K^+$ ($K_{ATP}$) channels and possibly voltage-gated $K^+$ channels. A recent patch-clamp study of rabbit cavernosal SMCs indicates two electrophysiological cell types, one that has predominantly voltage gated $K_{ATP}$ current and the other with predominantly $BK_{Ca}$ (Maxi) current.

Synthetic potassium channel openers such as nicorandil implicate $K_{ATP}$ channels in the regulation of tonic vasomotor activity. These agents, useful in the treatment of hypertension and angina, open $K_{ATP}$ channels, leading to potassium efflux, membrane hyperpolarization, and vasodilation. Thus drugs, which are potassium channel openers, alter membrane potential through $K_{ATP}$ channels and thereby activate voltage-dependent calcium channels producing changes in vascular smooth muscle contractility.

In addition to the large conductance calcium-sensitive K channel subtype (Maxi-K) and the metabolically regulated K channel subtype ($K_{ATP}$), recent studies also provide evidence for at least two other K channel subtypes. Although the $K_{ATP}$ and Maxi-K channel subtypes apparently account for much of the outward currents observed in cultured and freshly isolated human corporal smooth muscle cells, it would not be surprising if additional K channel subtypes were identified. There is also recent evidence for electrophysiological heterogeneity in the corporal smooth muscle cell population per se, and this could have important implications in erectile dysfunction and its therapy. In this invention, however, we have focused our investigations on physiologically most relevant K channel subtype to the regulation of corporal smooth muscle cell tone, namely the $K_{ATP}$ channel subtypes.

The activity of the $K_{ATP}$ channel subtypes in corporal smooth muscle is quite low at physiological membrane potentials in the absence of endogenous neurally mediated (i.e., erotic arousal) relaxation (i.e., at 40-50 mV, the open probabilities are estimated to be less than 1%. Moreover, recent studies have documented that the open probabilities of K channel subtypes are dramatically increased by the addition of prostaglandin E1 ("PGE1") (open probability approaches 1 with 33 μM PGE1) and pinacidil (a drug used to treat hypertension) at 10 μM respectively. The apparent quiescence of these channels in this cell type during flaccidity, and yet the ability of physiologically relevant stimuli to increase their activity so dramatically, make them attractive therapeutic targets, for whatever intervention.

In fact, clinical experience reveals that in the majority of patients, the etiology of erectile disorder is related to ion channel dysfunction, heightened contractility and/or impaired relaxation of the corporal smooth muscle and penile vasculature. The main physiological implication is that existing endogenous relaxing mechanisms are no longer able to elicit a degree of smooth muscle relaxation that is adequate to support the increase in blood flow and enhanced intracavernous pressure (ICP) required for the initiation and maintenance of penile erection.

It is the state of the art to appreciate that relaxation of the corporal smooth muscle is the key to the development of an erection, and that any future strategies that deal with the treatment of ED should focus on this target. The enhancement of smooth muscle relaxation may occur either by upregulating the production or activity of NO within the corporal tissues, or by developing a way to increase the relaxation process of corporal smooth muscle cells, or both. Stimulation of the $K_{ATP}$ channels in the cavernosal smooth muscle may be an effective way to modulate intracellular Ca levels and transmembrane Ca flux in this tissue and therefore enhance relaxation and improve erectile dysfunction.

The cardinal therapeutic question is whether or not it is possible to administer synthetic K channel activators systemically at concentrations that would have a greater impact on corporal smooth muscle K channels than on, for example, the vascular K channels in systemic resistance vessels. Stated more succinctly, the real challenge is to identify a therapeutic window or a specific agent that simultaneously satisfies two conditions. First, it must be effective as a K channel opener in the corpora, and second, that such therapeutic agent (which must perform successfully as a K channel corporal modulator) does not adversely affect vascular K channels in resistance vessels in other organs (e.g., affecting blood pressure), or coronary circulation.

The search begins with a simple truth. Drugs that raise cytosolic calcium either prevent or abort erection. Conversely, drugs that lower cytosolic calcium relax smooth muscle and can initiate penile erection. It is as simple as that, but clinical experience was not totally satisfactory.

Drugs acting through electromechanical mechanisms (voltage-gated channels) are primarily preferred as they can relax cavernous smooth muscle and trigger penile erection. Opening of the two types of $K^+$ channels in the penis, $K_{ATP}$ and large-conductance calcium-activated potassium (Maxi-K), will achieve the desired target; hyperpolarize the cavernous smooth muscle cell to result in relaxation. Yet, such therapeutic approach is hardly free of systemic side effects.

Interventions in the corporal vascular sinuses would have to be sufficient to ensure that when the K channels are activated by the addition of neural signals, (i.e., through erotic arousal) an enhanced hyperpolarization and a corporal smooth muscle cell relaxation occurs (provided there is a combined effect of mind and channels).

Several $K^+$ channel openers (pinacidil, cromakalim, lemakalim, and nicorandil) have been shown to be effective in vitro in causing relaxation of isolated cavernous tissue from both animals and man, and to produce erection when injected intracavernously (a very invasive and hardly tolerated procedure) in monkeys and humans. However, only minoxidil, the arteriolar vasodilator used in patients with severe hypertension, seems to have been tried orally in man. Minoxidil is a drug not active in vitro but is metabolized in the liver to the active molecule, minoxidil NO sulfate. It has been shown that minoxidil sulfate has the properties of a $K^+$ channel opener, its side effects are remarkable.

The preliminary experiences with minoxidil seem promising in at least demonstrating the principle that "opening" modulation in significant $K^+$ channels, promotes the process of erection. However, in testing the efficacy of PCO ($K^+$ channel opener) as antihypertensive agents, it was also observed that they produced changes in the T-wave of the patient's electrocardiogram (flat, inverted or biphasic). Thus their effects on the heart cannot be ignored (when we applied our own experimental WMF radiation on intact pigs we observed similar changes when the field was aimed at the heart).

One way or another, the treatment of ED has seen its most dramatic improvement over the past five years using drugs of a completely different family. The introduction of the first effective, well-tolerated oral agent for erectile dysfunction began in 1998 with the introduction of sildenafil for the treatment of ED. Sildenafil, a phosphodiesterase type-5 (PDE5) inhibitor, blocks the enzyme PDE5 in the corpus cavernosum smooth muscle. This permits the secondary neurotransmitter, cGMP, to persist longer and be present in higher concentrations, facilitating relaxation of the corpus cavernosum smooth muscle and hence the erectile function. This and other PDE5 agents facilitate erections and produce successful improvement in erectile function in more than 70% of men treated for erectile dysfunction.

The market for PDE5 have recently been expanded by two unique new compounds: vardenafil and tadalafil. These two agents, whose profiles are different from sildenafil, are now approved in the United States, Europe, Canada, and most countries throughout the world. Vardenafil, a unique agent similar in its chemical structure to sildenafil, is a highly potent PDE5 inhibitor with a rapid onset and good efficacy and tolerability. The PDE inhibitors intervene in the cascade leading to erection two steps above the stage where potassium channel openers intervene (as well as our electromagnetic fields). Thus, the use of PDEs such as sildenafil does not interfere with the favorable effect of the WMF of the present invention, on the contrary, both forms of therapy can act in synergy.

Precise modulation of cavernosal (corporal) smooth muscle tone is central to the development of effective and improved treatments for ED. Relaxation of corporal smooth muscle is accomplished by lowering of cytosolic calcium ($Ca^{2+}$), which is mediated by several mechanistic pathways. One of the mechanisms involves hyperpolarization of corporal smooth muscle cells via activation of potassium channels. Corporal smooth muscle cells express several different $K^+$ channels of which Maxi-K and $K_{ATP}$ channels were found to be the most prominent subtype. Thus, activation of Maxi-K or $K_{ATP}$ channels present in corporal smooth muscle represents an important and attractive mechanism for controlling corporal smooth muscle function.

Activation through membrane hyperpolarization closes the voltage-gated $Ca^{2+}$ channels with a consequent of lowering cytosolic $Ca^{2+}$ and producing relaxation of corporeal smooth muscle. Different modulators of corporal smooth muscle tone have all been targeted. The ultimate goal is to create an "on demand" effective relaxation signal adequate to promote sufficient relaxation of corporal smooth muscle to permit erection, and to achieve that without compromising other body systems. It is pointed out once more that although sildenafil selectively affects the penile corpora cavernosa, it is nevertheless a systemic agent (orally ingested) and therefore affects the patient's blood pressure and cardiac function, particularly in patients who are maintained on nitrates. It is undesired that such patients use sildenafil together with nitrates, and may it be deleterious if they suddenly stop the use of nitrates for the sake of consuming sildenafil.

Experimental Work

From the background data it was evident that a preferred therapeutic intervention will be such that possess the ability to close voltage gated $Ca^{2+}$ L-type channels, either directly, or indirectly via potassium channels. Such was the intervention the inventors looked for, discovered, and tested: ultraweak pulsating magnetic fields of low frequency (about 15.9-16

Hz), that when applied to the penis functions as "virtual" local drug, affecting large conductance potassium channels and leading to the blockage of calcium ion entry to the myocyte culminating with vascular dilation.

In order to validate the mechanism of action of WMF on modulating $K^+$ channels, modulated fields were tested by applying modulated fields in vivo to the hearts of pigs and rats and also by applying the modulated fields to isolated rat muscle cells in tissue culture. Among the changes were shortening of the PR interval in pigs and the P wave duration in rats These changes are typical to $K_{ATP}$ channel opening effect. Echocardiographic studies done on rats demonstrated diminished myocardial contraction at the intenventricular septum, which points at reduction of intracellular calcium ions, following the application of WMF. For the cells in culture, there was significant reduction in the concentration of calcium ions in the cells, and diminished contraction. The $Ca^{2+}$ concentration within the individual cells was observed and quantified to be reduced following the application of the pulsed ultraweak magnetic fields as $Ca^{2+}$ shifted out of the muscle cells resulting in significant reduction in contraction (i.e. relaxation).

Following such promising studies, experiments on men had very favorable results. Twenty minutes following treatment, the average penile temperature of ten men increased from 34.4° C. to 35.5° C., which resulted from marked increase in blood flow, which preceded erection.

From the Macro to the Micro:

Myocite Cell Culture in Eight Experiments: Rat hearts (1-2 days old) were removed under sterile conditions and washed, then minced and agitated in solution of proteolytic enzymes. The cells were separated from the solution, cultured and reviewed under microscope to assess intra-cellular calcium measurements using indo-1-fluorescence, which was bound to $Ca^{2+}$. The $Ca^{2+}$ efflux and influx out of and into the cell was measured before and after the application of ultraweak magnetic field at about 16 Hz and about 8 Hz. With WMF field application (at about 60 pT) there was remarkable shift of $Ca^{2+}+$ out of the cells to the interstitial surrounding, and the myocytes significantly declined its force of contraction, (i.e., increased relaxation of SMCs).

Such mechanism is of particular interest since by its non-linear cooperative effect, which is the entraining of weak non-thermal sub-threshold signals of the ion channels through weak but pulsed magnetic fluctuation, it amplifies the $K_{ATP}$ channels to a threshold substantial enough to open, and close in turn, $Ca^{2+}$ channels to reduce cellular $Ca^{2+}$ and precipitate relaxation. It should be noted that the myocardium has $K_{ATP}$ channels but not Maxi-K ($K_{Ca}$) channels. In contrast, the corpora cavernosa smooth muscle cells and SMCs in the vascular system have both $K_{ATP}$ and Maxi-K channels. Thus, from our cardiac different studies we verified that WMF affects the penis through $K_{ATP}$ channels and it could affect Maxi-K channels as well.

Elucidation of the Effect (1) Biological Effects of WMF

The interaction of electromagnetic fields with biological systems is of interest not only because of fundamental scientific curiosity, but also because of potential medical benefits.

Schwartz et al. (1980) found that when frog hearts are exposed to a 240-Mz EM field, which was modulated at 16 Hz (the window effect), a field-dependent change was observed in efflux of $Ca^{2+}$ ions from the cell.

Field intensity and modulation frequency were shown to be important determinants in WMF causing cellular $Ca^{2+}$ efflux. Since a WMF produces significant effects, and the modulation frequency is critical for that matter, its effect which is not thermal, must be purely biological, an intervention acting at the cellular level to influence cellular functions.

At any rate, the mechanism of activation of $K_{ATP}$ and Maxi-K channels must be similar to the ability of certain drugs (such as potassium channel openers: minoxidil and nicorandil) to induce efflux of $Ca^{2+}$ from the smooth muscle cells of the corpora initiating relaxation (which precipitate erection).

As demonstrated in pig, rat and tissue culture experiments, WMF modulated at 16 Hz is capable of affecting the animal to promote its $K^+$ channels to induce reduction in cellular $Ca^{2+}$ and relaxation.

The rational for selecting such effect for augmenting erection was therefore sound and true. The inventors checked the effect of the WMF through its application on different tissues, in vivo and in vitro, to validate that it possesses the effect of a $K^+$ channel opener.

Clinical application of the procedure achieved complete or partial remedy in most patients who use it. In some, particularly diabetics, its favorable effect was assisted by utilization of sildenafil (50 or 100 mg) consumed an hour before. Like in the case of sildenafil, the effect of the device is conditional with existent erotic arousal.

In the case of ladies who tried the flat transducers (see below), the users claimed that activation induced certain pleasant tingling sensation that some defined as sexually arousing.

(2) Detailed Mechanism of how WMF Affects the $K^+$ and $Ca^{2+}$ Channels

In a pig, the simultaneous and instantaneous appearance of PR shortening and QT lengthening (both by about 40 ms) within two minutes following the application of a tiny sinusoidal field modulated at about 16 Hz was unique in nature. There are multiple $K_{ATP}$ channels in the AVN His-purkinje system. Theoretically, the WMF effect to shorten the conduction system's action potentials and enhance velocity throughout the A-V junction must be dependent on $K_{ATP}$ channel activation.

The WMF used in the experiments was indeed very weak. To clarify: It was about one thousandth of the magnetic intensity of the earth's geomagnetic field. In the game of stimulating excitable tissues via magnetic fields, there is a "window effect" i.e., bigger is not better. Excitable cells are not motivated to yield to loud messages. Fields of high intensity are barred from entering and resonating with channel dipoles. High-intensity signals of external noise are counterproductive since they suffocate the channel's minute inherent signals. The mechanism through which an extremely weak external magnetic field modulated by periodic stimulus (16 Hz), can be intercepted by the channels while larger signals are ignored must be that of stochastic resonance ("SR").

(3) How the Ultraweak Prevails

In everyday life, noise is generally viewed as being a harmful influence that hampers the detection and transfer of information. It is now accepted that noise can enhance the response of a system to weak signals, via a mechanism known as stochastic resonance ("SR"). This is an intuitively paradoxical phenomenon in which the signal-to-noise ratio ("SNR"), when detecting or transmitting a signal can be enhanced by noise. Injection of optimal amount of noise into an excitable system increases the quality of the signal received via the noise-induced synchronization.

The original term "stochastic resonance" was coined in 1981 by Benzi et al to explain a long-standing paradox in climatology: What causes the almost periodic recurrence of the primary cycle of ice ages every 100,000 years or so? There is also a periodically recurring wobble in the Earth's orbit around the sun, approximately once every 100,000 years, which is related to the timing of glaciations. Yet this perturbation is far too weak to cause a deterministic freeze. It is a very weak signal that is embedded in the much stronger noise caused by the annual and even daily swings in the amount of energy received, retained and reflected back to the sun. The researchers proposed that the above strong fluctuations (noise) are able to amplify the embedded weak periodic signal when they act together in a synergetic manner, every 100,000 years or so.

Within the last ten years, researchers have become aware that SR is a fundamental and general principle of biological information processing. Some animal's acute sensitivity and ability to detect weak coherent signals was assumed to be related to the molecular mechanisms of biological SR that have their roots in the stochastic properties of the ion channel arrays of receptor cell membranes.

In SR, the maximum enhancement of the output SNR occurs when the noise induced rate, such as the switching rate of a bistable system like that of the ion channels (which could be in either an open or a closed position) matches the frequency of the subthreshold periodic stimulus. This was regarded as a true resonance because there is a matching set of time scales (or frequencies) and the results were obtained in a bistable model and thus represent a "bona fide" resonance.

SNR reaches its maximum when the intensity of the external noise is properly tuned to the internal parameters of the particular biological system.

In the present experiments, injection of near threshold deterministic, periodic signal, such as sinusoid waveform modulated at or about 16 Hz (rather than simple random noise) to the external stimulating WMF input, could achieve an amplified sensitivity in SNR output.

In order for periodic SR to be effective three minimal conditions must be present, and indeed all were present in the present experiments:

a) a source of background noise, b) generally weak coherent input, (such as a sinusoid signal possessing the "right" frequency=about 16 Hz, some effect to 8 Hz, 32 Hz).

c) a characteristic sensory barrier or threshold that the basic system (ion channels) has to overcome in order to perform its usual (open-close) task.

It is therefore that a dynamic system such as the ion channels, has an option to respond in resonance, which is absent when either the periodic forcing (i.e., our external signals occurring every about 62.5 ms) or the background perturbation, do not exist.

Most likely, SR mechanism originated in biological systems as soon as the stochastic properties of primitive $K^+$ channels located in the most archaic bacteria evolved 3.3 billion years ago. During evolution, the SR concept developed to exhibit a general organizing principle for the cell membrane system in parallel with the emergence of more sophisticated ion channels.

Ion-channel fluctuations are an inherent phenomenon and are caused by the random opening and closing of gates in compliance with the rules of quantum mechanics and is thought to be caused by thermal hopping of the channel protein between different conformational states.

The channels behave in what can be regarded as capricious manner, sometime they open quickly, sometimes more slowly. Sometimes they open briefly and sometime for a longer period. However, for a larger number of channels, the common membrane voltage of the action potential couples the random opening and closing event more tightly, resulting in collective events of a significant cluster of any available channels at the same time. If we add the behavior of all the channels that work together, we get an ensemble of ion currents that are equivalent to the macroscopic currents we eventually observe in the ECG (such as was observed in the pigs whose heart were exposed to WMF). The collective obtained enhancement is caused by the massive synchronization of a whole channel array and is reached whenever the noise intensity is properly tuned to the coupling between neighboring oscillating channels. The SMCs in the penile cavernous body are connected to each other by channels to make a spongious syncithium where each cell is connected to those which surround it by ions and electromagnetic channels they are called gap-junctions which are replace of those in the heart.

A rotation of a single charge amino acid in one channel's protein might generate an electromagnetic field that entrains rotation of a corresponding amino acid in a second protein belonging to a neighboring channel in a neighboring cell, provided it occupies a critically close enough position. The second channel reacts with an electromagnetic field of its own that could affect neighbor cells, provided they, too, are in extremely close proximity. The WMF impulses in both heart and penis may spread in a pattern that is characterized in forest fires, where flames which propagate in random materials turn to advance in epidemic speeds. It is only the "big" flame i.e. erection, that is felt from the observation post above.

BRIEF DESCRIPTION OF THE INVENTION

The present invention generally relates to methods and apparatus for the application of pulsed, weak electromagnetic fields to the penis to enable essential erectile function recovery by potentiating penile erection. Another aspect of the invention relates to methods and apparatus for the application of pulsed weak electromagnetic fields to an area of a women having a medical condition. For example, applying the magnetic field to the lower pelvic region of a woman in order to promote sexual arousal or to treat urinary incontinence.

In accordance with various embodiments of the invention, the apparatus generates a pulsed or modulated "ultraweak" (i.e. not more than about 5 microtesla in the volume occupied by the penis or, alternatively, a peak intensity in a magnetic coil of a transducer, of about 100 nanotesla or more) electromagnetic field which is directed at a penis in order to potentiate erection. Preferably, the frequency of the modulated or pulsed electromagnetic field is about 15.94 to about 16 hertz with a waveshape that is sinusoidal. An apparatus structured according to the basic principle of the present invention modifies the magnetic coil current to achieve the desired frequency, amplitude and waveshape.

Without wishing to be bound by any theory or mechanism, it is believed that the application of a pulsed, ultraweak electromagnetic field to the penis potentates erection by affecting the $K^+$ and $Ca^{2+}$ channels, inducing them to change their conformation by moving from one certain state (activation) to another (inactivation), or vice versa. The rational of the therapy is to promote organ function by preventing/reducing intra-cellular calcium accumulation, thus improving smooth cell relaxation and promoting erection.

DETAILED DESCRIPTION OF THE INVENTION

Figure 1:
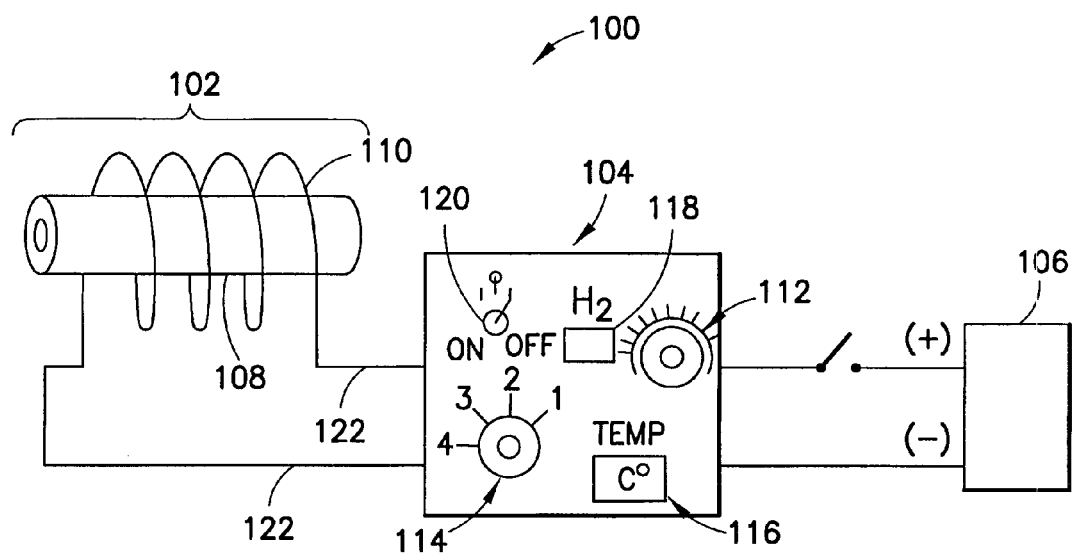
FIG. 1 is a drawing depicting an apparatus for potentiating penile erection in accordance with one embodiment of the invention.

Referring to FIG. 1, in a preferred embodiment of the present invention, an apparatus for potentiating (i.e., for promoting or encouraging) penile erection 100 is generally made up of a transducer 102, a controller-oscillator 104, and a power source 106. The power source supplies power to the controller-oscillator which, in turn, generates and sends electrical signals (i.e. electrical current having a voltage, frequency, amplitude and waveform controlled or regulated by the controller-oscillator) to the transducer. The transducer transduces the electrical signal into a pulsating or modulated weak magnetic field.

The transducer 102 is made up of a tube 108 having a magnetic coil 110 mounted, wrapped or wound around the external surface of the tube. The tube 108 is generally a hollow, cylindrical-shaped tube, preferably flexible. The tube 108 is made from a non-metallic, non-conductive material such as plastic. The tube is "dimensioned" (i.e., sized, shaped, constructed and arranged) to be able to comfortably hold or contain a fully erect penis therein. A temperature sensor (not shown) such as a thermistor may be mounted on the tube to measure the temperature of the penis. The tube helps to support the magnetic coil and also serves to protect the penis.

The magnetic coil 110 is made from a wire-type material that is electrically conductive, for example, copper wire. The magnetic coil is wound or wrapped around the outside surface of the tube in a spiral-like manner like a spring. The magnetic coil may be embedded within the material of the tube. The magnetic coil is connected to the controller-oscillator by leads 122. Upon energization of the magnetic coil by electrical signals or current from the controller-oscillator, the magnetic coil produces a magnetic field.

The controller-oscillator 104 provides the electrical signals or current to the transducer. Preferably, the controller-oscillator has a frequency controller 112 for controlling the frequency of the pulsating magnetic field, an amplitude controller 114 for controlling the intensity of the magnetic field; a temperature readout display 116 for showing the temperature of the penis; a frequency display 118 for showing the frequency of the pulsating magnetic field and an on/off switch 120 for turning the apparatus on or off.

The power source 106 supplies the electric power to the controller-oscillator and, if needed, also supplies power to other devices (e.g., vibrator, buzzer). The power source is preferably a battery. The power source may be mounted inside the controller-oscillator or attached to the controller-oscillator as a separate unit.

To use the apparatus, the penis is inserted into the tube and the apparatus is turned on. The pulsating magnetic field produced when the apparatus is activated is directed along the length of the penis and around its circumference. The magnetic field has an intensity of not more than about 5 microtesla in the volume occupied by the penis or, when measured in the magnetic coil, a peak intensity, of about 100 nanotesla to about 500 nanotesla or more. The frequency of the magnetic field is between about 8 hertz and about 64 hertz, preferably about 15.94 hertz and about 16 hertz. The waveshape is sinusoidal. Once the penis is fully erect, the apparatus is turned off, the tube removed and sexual intercourse commences.

In another embodiment (FIG. 2), the transducer of the apparatus 200 is a carry-it-through transducer 202 that is made up of a collar 208 and magnetic coil 210. The collar is basically a tube having a short length and formed in the shape of a ring. The magnetic coil 210 is wound around the collar 208 in the same manner as the magnetic coil 110 of FIG. 1. The ring-like carry-it-through or short transducer 202 is designed to be mounted or worn around the root of the penis (i.e., its most proximal section) to allow the continuous utilization of the device "on line", i.e., during sexual intercourse.

The collar 208 is preferably about 2 cm. long and has a diameter sufficient to encircle the base of the penis at the junction of the pubis, preferably about 4 to 5 cm. The collar is made from a non-conductive, non-metallic, elastic and, preferably, light material such as plastic. The transducer is dimensioned to allow it to adapt concomitantly in size with the dilation of the penis. Thus, the collar 208 is preferably made from an elastic material that is sufficiently pliable to allow the collar to accommodate a fully-erect penis. The magnetic coil 210 is made from a wire-type material that is electrically conductive and also sufficiently elastic to allow the magnetic coil to adjust in size as the penis becomes erect or more 100% increase in penile diameter.

The controller oscillator 204 is dimensioned to be a minute and compact unit in order to allow it to be mounted on the collar 208. The power source (not shown) is also a small and compact unit, e.g. a tiny battery like a watch battery that is also mounted on the collar 208 and may be mounted inside the controller-oscillator. A thermistor (not shown) and a buzzer-vibrator 218 may be attached to the collar 208. The thermistor is in contact with the ventral surface of the penis and the buzzer-vibrator 218 signals when the penis temperature, as measured by the thermistor reaches a certain optimum for the promotion of intercourse. Preferably, power source provides a minute current (preferably on the order of about 1 mA or less) so that the coils do not drain the battery. The power source also supplies power to the thermistor and buzzer vibrator.

To use the apparatus 200, the penis is inserted into the collar 208 and the collar is moved to the root of the penis and the apparatus is activated. The pulsating magnetic field produced when the apparatus is activated, is directed along the length of the root of the penis and the circumference of the penis's root. The magnetic field has an intensity of not more than about 5 microtesla in the volume occupied by the penis or, when measured in the magnetic coil, a peak intensity, of about 100 nanotesla to about 5 microtesla. The frequency of the magnetic field is between about 8 hertz and about 64 hertz, preferably about 15.94 and about 16 hertz. The waveshape is sinusoidal. Once the penis is fully erect, sexual intercourse can commence without the apparatus having to be removed or the apparatus being turned off.

Figure 2:
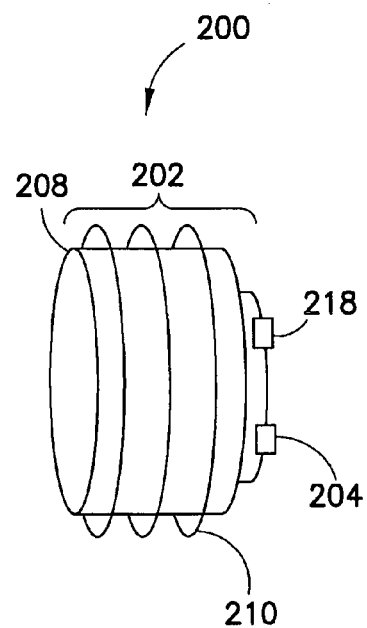
FIG. 2 is a drawing depicting an apparatus for potentiating penile erection in accordance with another embodiment of the invention.

In an alternate embodiment, not shown, the carry-it-through transducer may be connected to the distal end of a condom. A magnetic coil similar to the magnetic coil 210 of FIG. 2 is embedded within the material of the condom and is connected to a controller-oscillator.

Figure 3:
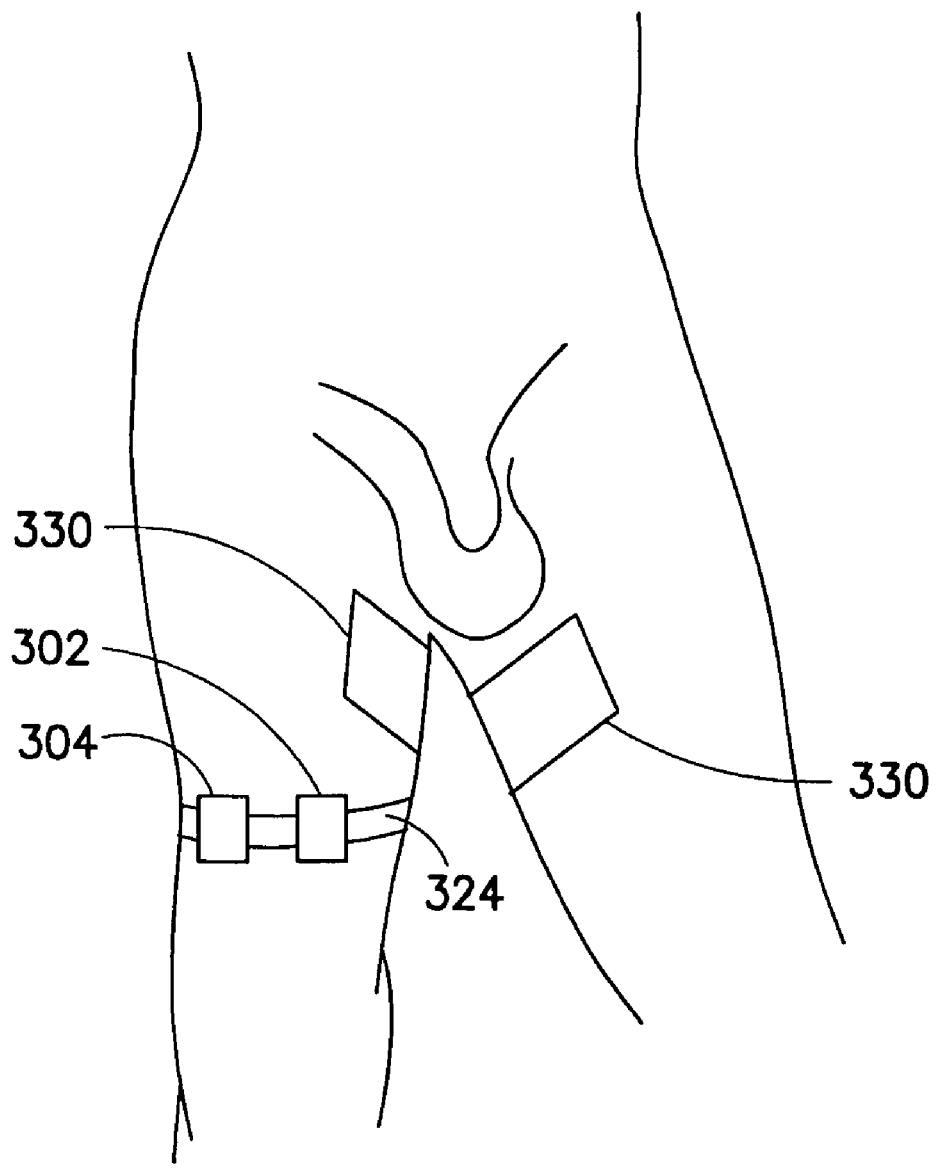
FIG. 3 is a drawing depicting an apparatus for potentiating penile erection in accordance with a further embodiment of the invention.

Another embodiment of an apparatus embodying the features of the present invention is shown in FIG. 3. In this embodiment, the apparatus comprises a controller-oscillator 304 having a power source, an active transducer 302 and one or more remote passive transducers (not shown). The controller-oscillator is similar to the controller oscillator 104 discussed above with respect to FIG. 1, but preferably, dimensioned to be smaller and lighter. The passive transducer is constructed and assembled using methods and materials that are well-known and may include a flat magnetic coil or, alternatively, multiple flat, minute magnetic coils. The active transducer and passive transducers are constructed and assembled using methods and materials that are well-known.

The controller-oscillator 304 and active transducer 302 are mounted or attached to a strap 324 worn by a user around the thigh. Alternatively, the controller-oscillator and active transducer may be attached to a belt (not shown) worn around the waist of the user. The remote transducers are attached to the inner surface of the thighs, adjacent to the penis using attachment means such as belts, straps, pouches, but preferably using medical adhesive patches 330. This configuration has certain advantages in the event the user practices sex out of his usual residence, and thus, the user carries the apparatus with him wherever he goes.

In use, the active transducer generates a pulsating magnetic field. Since the active transducer is not located near the penis, the magnetic field is described as being remotely generated from the penis, that is, generated or originating at a distance away from the penis. This pulsating magnetic field is received by the passive transducer. As a result of induction, the passive transducer, in turn, re-directs or re-transmits this magnetic field to the penis. The pulsating magnetic field has an intensity of not more than about 5 microtesla in the volume occupied by the penis or, alternatively, when measured in the surroundings. The frequency of the magnetic field is between about 8 hertz to about 64 hertz, preferably about 15.94 to about 16 hertz. Once the penis is erect, sexual intercourse can begin without the apparatus having to be turned off or removed.

The foregoing apparatus is constructed to be friendly to the user, relieving him of the inconvenience of having devices mounted on his organ while being involved in sexual contact. The operation of this apparatus is achieved discretely by manipulating the controller-oscillator mounted on the belt which leaves the penis bare from any attachments. As such, the individual's partner is oblivious that her mate is assisted by an electromagnetic field.

Figure 4:
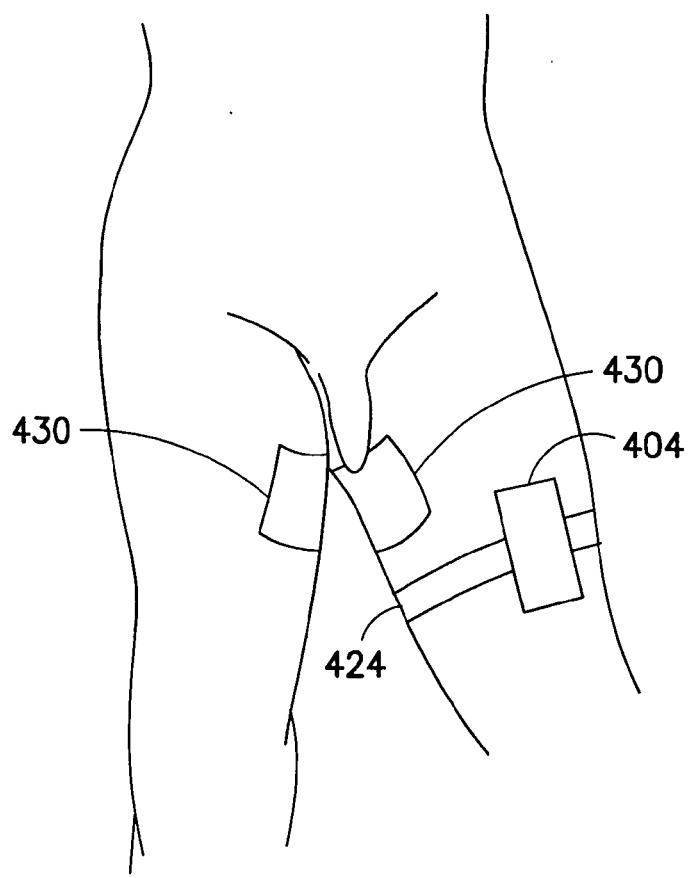
FIG. 4 is a drawing depicting an apparatus for potentiating penile erection in accordance with another embodiment of the invention.

Another embodiment is shown in FIG. 4. Here, the apparatus comprises a combined controller-oscillator, active transducer unit and power supply, hereafter called a remote generator-controller 404 and one or more passive transducers worn by the user. The controller-oscillator, active transducer unit, remote transducer and power supply are similar to and function in the same manner as the controller-oscillator 304, active transducer 302, passive transducer and power supply described in FIG. 3. The remote generator-controller and passive transducers are constructed and assembled using methods and materials that are well-known The remote generator-controller 404 is constructed, adapted and arranged to produce a pulsating magnetic field that can affect the remote transducer at a distance, preferably up to a range of about 10 centimeters. The remote generator-oscillator is mounted to the thigh of the user by attachment means such tape, pouch, belt, or a strap 424. The passive transducer is attached to the thigh, adjacent to the penis with attachment means such as adhesive patches 430.

In use, the remote generator controller generates a pulsating magnetic field. Since the remote generator-controller-oscillator is not located near the penis, the magnetic field generator is "remotely generating" a magnetic field, that is, it is generating a magnetic field at a distance away from the penis. The pulsating magnetic field has an intensity of not more than about 5 microtesla in the penis or when measured in its peak intensity. The frequency of the magnetic field is between about 0.2 Hz and about 300 Hz, preferably about 15.94 hertz and about 16 hertz. This pulsating magnetic field is received by the passive transducer. As a result of induction, the passive transducer, in turn, re-directs or re-transmits this magnetic field to the penis. Once the penis is erect, sexual intercourse can begin without the apparatus having to be turned off or removed.

Figure 5:
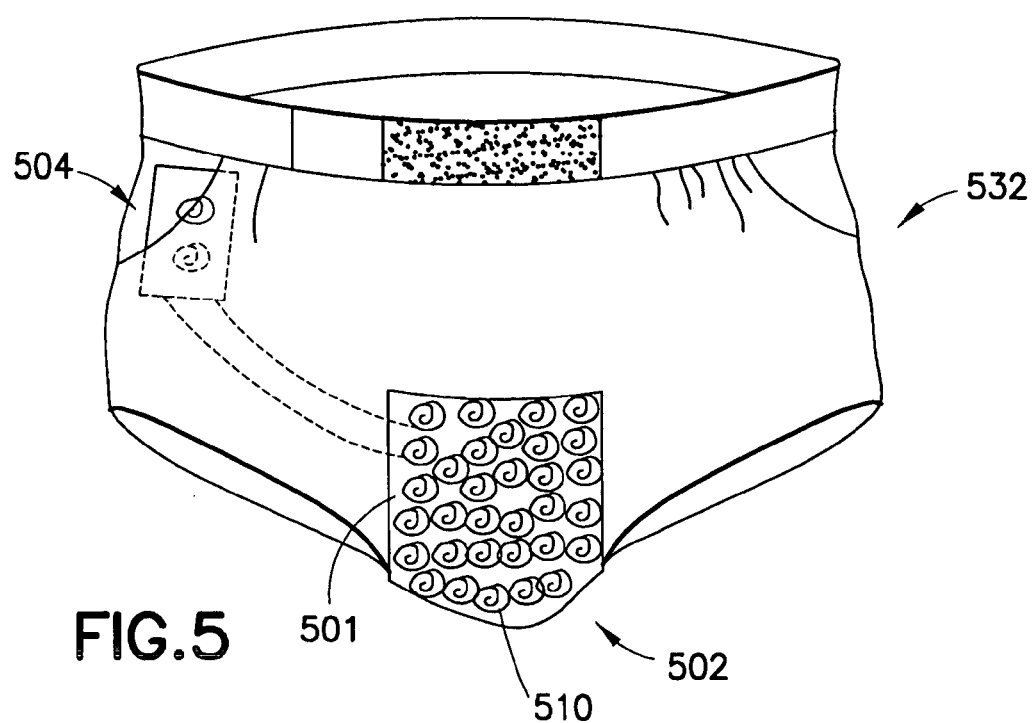
FIG. 5 is a drawing of an apparatus for use by women in accordance with one embodiment of the invention.

Referring to FIG. 5, another aspect of the invention relates to an apparatus for treating medical conditions or diseases in women (for example, treating sexual dysfunction by promoting sexual arousal or treating incontinence) by directing a pulsating magnetic field to the affected area or portion of the woman (e.g. the pelvic area in case of incontinence or sexual dysfunction).

The apparatus comprises a patch transducer 502 for generating a pulsating magnetic field and a controller-oscillator 504 having a power supply. The transducer 502 is connected to the controller-oscillator by leads. The apparatus may also have a temperature sensor (not shown) for measuring body temperature.

The controller-oscillator 504 is similar to the controller-oscillators 104, 204 previously described above with respect to FIGS. 1 and 2. The patch transducer 502 comprises a generally rectangular shaped flat patch 501 made from a non-conductive material, preferably sized about 10 cm.×15 cm. Multiple flat magnetic coils 510 (preferably having a diameter of about 15-20 mm) are attached or mounted to the patch by attachment means such as glue or sewing. The flat magnetic coils 510 are made from a conductive material such as copper and are attached by the leads to the controller-oscillator. In a one embodiment, to treat sexual dysfunction or incontinence, the patch transducer is mounted near the bottom of ladies underwear such as panties 532, adjacent to the pelvic region using attachment means, such as Velcro® or sewing.

In use, the controller-oscillator 504 generates electrical signals which are sent to the patch transducer which, in turn, transduces these signals into a pulsating magnetic field directed at the pelvic region. The pulsating magnetic field has an intensity of not more than about 5 microtesla and a frequency of between about 4 hertz and about 128 hertz, preferably between about 15.94 hertz and about 16 Hz.

While the invention has been described with reference to particular embodiments, it will be understood by those skilled in the art that various changes may be made and equivalents may be substituted for members thereof without departing from the scope of the invention, In addition, modifications may be made to adapt a particular situation to the teaching of the invention without departing from the essential scope thereof. Therefore, it is intended that the invention be not limited to the particular embodiment disclosed as the best mode for carrying out this invention, but that the invention will include all embodiments falling within the scope of the appended claims.

What is claimed is:

1. An apparatus for potentiating penile erection, the apparatus comprising:
    an active transducer for transducing electrical signals into a pulsating magnetic field, wherein the magnetic field is remotely generated and further, wherein the magnetic field has a frequency of between about 15.94 hertz to about 16 hertz;
    at least one passive transducer for receiving the magnetic field and re-directing the magnetic field to a penis,
    a controller-oscillator for generating and controlling the electrical signals; and
    a power source.

2. An apparatus for potentiating erectile function, the apparatus comprising:
a remote generator-controller for remotely generating a pulsating magnetic field, the remote generator-controller comprising:
a controller-oscillator
a transducer; and
a power source; and
at least one passive transducer for receiving the magnetic field and re-directing the magnetic field to a penis, wherein the magnetic field has a frequency of between about 15.94 hertz to about 16 hertz.

3. A method for potentiating penile erection, the method comprising:
remotely generating a pulsating magnetic field using an active transducer; and
receiving and re-directing the pulsating magnetic field towards a penis using a passive transducer,
wherein the pulsating magnetic field has a frequency of between about 15.94 hertz to about 16 hertz.

* * * * *